Figure 1A:
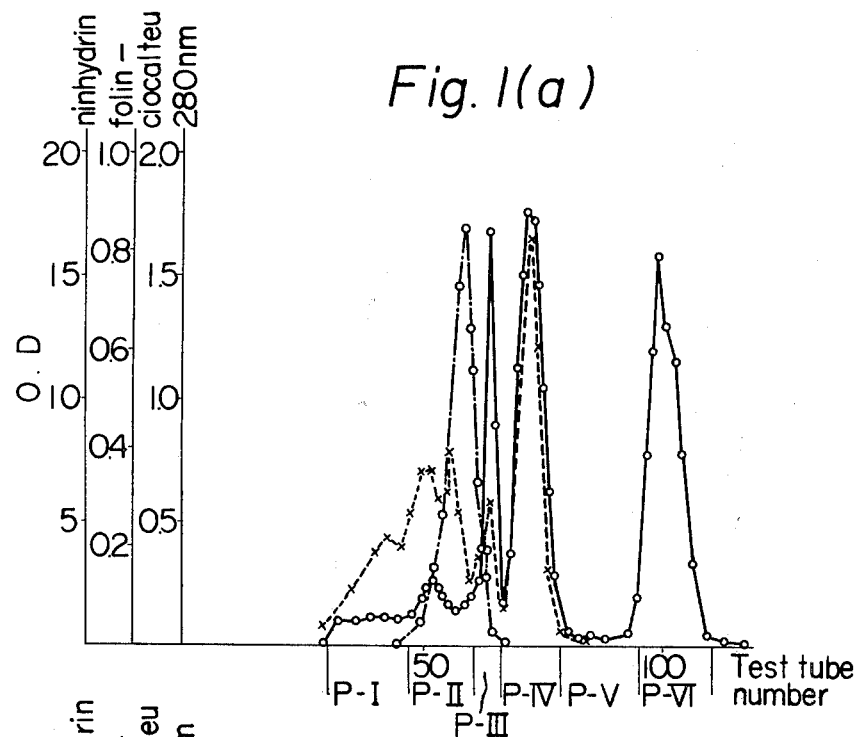

United States Patent [19]

Ishii

[11] 4,067,963

[45] Jan. 10, 1978

[54] SUBSTANCE ACTING TO PREVENT AND IMPROVE CEREBRAL FUNCTION DISORDER AND PROCESS FOR PREPARING THE SAME

[75] Inventor: Shozo Ishii, Tokyo, Japan

[73] Assignee: Chugai Seiyaku Kabushiki Kaisha, Tokyo, Japan

[21] Appl. No.: 592,346

[22] Filed: July 1, 1975

[30] Foreign Application Priority Data

Jan. 7, 1974 Japan .................................. 49-74303

[51] Int. Cl.$^2$ .................... A61K 35/12; C12D 13/06; C12B 1/00
[52] U.S. Cl. .................................... 424/95; 424/177; 195/29; 260/112 R; 260/119; 424/115
[58] Field of Search ............... 195/29, 30; 260/112 R, 260/119; 424/95

[56] References Cited

U.S. PATENT DOCUMENTS

| | | | |
|---|---|---|---|
| 1,851,253 | 3/1932 | Kahn | 195/29 |
| 2,110,613 | 3/1938 | Swenson | 195/29 |
| 2,280,147 | 4/1942 | Fischer | 195/29 |
| 2,350,811 | 6/1944 | Percheron | 260/112 R |
| 3,720,763 | 3/1973 | Ishii | 424/95 |
| 3,794,561 | 2/1974 | Matsukawa et al. | 195/29 |
| 3,855,196 | 12/1974 | Matsukawa et al. | 195/29 |

*Primary Examiner*—Donald B. Moyer
*Attorney, Agent, or Firm*—Browdy and Neimark

[57] ABSTRACT

Substance acting to prevent and improve cerebral function disorder which is prepared by treating albumin with a fatty acid and hydrolizing the modified albumin is described.

7 Claims, 5 Drawing Figures

Incubation time of mitochondria of rat brain (a)

(b)

(c)

(d)

(e)

(f)

(a)

(b)

(c)

(d)

(e)

(f)

SUBSTANCE ACTING TO PREVENT AND IMPROVE CEREBRAL FUNCTION DISORDER AND PROCESS FOR PREPARING THE SAME

This invention relates to a substance acting to prevent and improve cerebral function disorder and a process for preparing the same.

The inventor of this invention, from his observations of brain cell swelling resulting from injury of brain cells, noted that the activity of adenosin triphosphatase in brain mitochondria rapidly decreases and the swelling of brain tissue and mitochondria occurs dependently. Then the inventor enlarged the scope of his study to include the relationship between swelling of brain cells and the function of brain mitochondria. He found that bovine serum albumin also inhibits swelling of mitochondria as well as protects dinitrophenol dependent adenosine triphosphatase (referred to as DNP-ATPase) from inactivation, just as a mitochondrial extract of an animal brain taken out immediately after slaughter, and also that said bovine serum albumin acts to restore cerebral functions, and is especially effective in restoring a patient to consciousness.

The inventor has continued the study and found that the activities mentioned above are not observed on egg albumin per se but are unexpectedly observed on hydrolizate of egg albumin and that the active substance can be more easily obtained in high purity from egg albumin if egg albumin is chemically combined to a fatty acid of relatively high molecular weight and if the combined material is hydrolyzed with a protease. Also, it has been found that this technique for obtaining the active substance from egg albumin can be applied for any type of albumin, such as bovine serum albumin.

The object substance of this invention exhibits in general characteristics similar to those of a peptide, and the following physical and chemical properties have been confirmed.

1. Appearance and Properties:
   Colorless and Odorless
2. Solubility:
   Easily soluble in water, Hardly soluble in alcohol, acetone, and ether
3. Stability:
   Stable at room temperature, Stable under freezing and defrosting
4. Ultraviolet Absorption Spectrum:
   Maximum absorption at 280 nm
5. Molecular weight:
   1000 ~ 3000 (Gelfiltration)
6. Color Reaction:
   Positive in ninhydrin, folin-ciocalteu and biuret reactions.
   Negative in anthron, orcinol and Elson-Morgan's reactions.
7. Thin Layer Chromatography:
   RF = 0.355 ± 0.075
   Plate: microcrystalline cellulose
   Developing Solvent: n-butanol:acetic acid:water = 3:1:1
   Conditions for Developing: Room temperature,
   Color Reaction: ninhydrin FIG. 1-(a) shows the elution curve in Example (with fatty acid treatment).

Figure 1B:
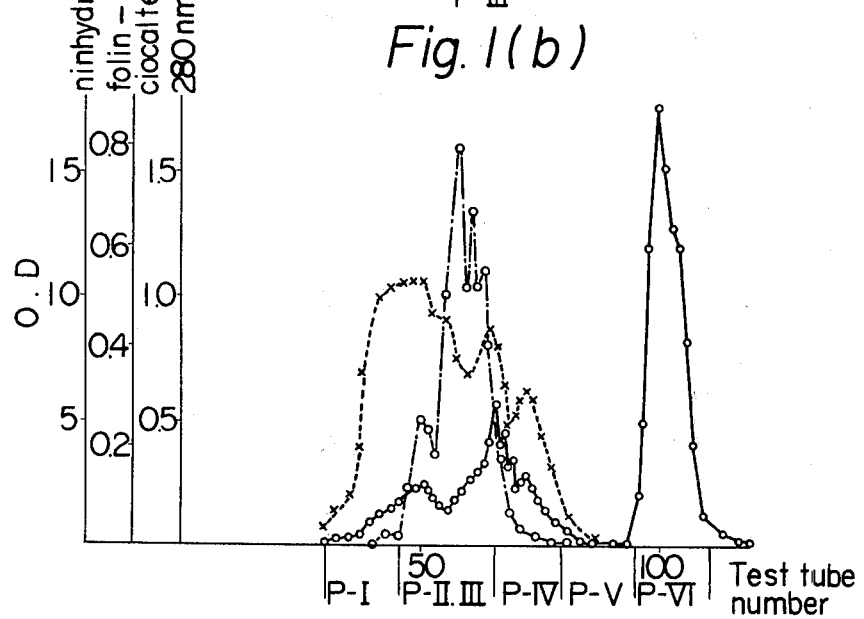

FIG. 1-(b) shows the elution curve in Example (without fatty acid treatment). In these FIGS., the curves are defined as follows:

| | |
|---|---|
| —·—o—·—: | absorbance at 570 nm (ninhydrin reaction) |
| ———x———: | absorbance at 650 nm (folin-ciocalteu's reaction) |
| ———o———: | absorbance at 280 nm |

Figure 2:
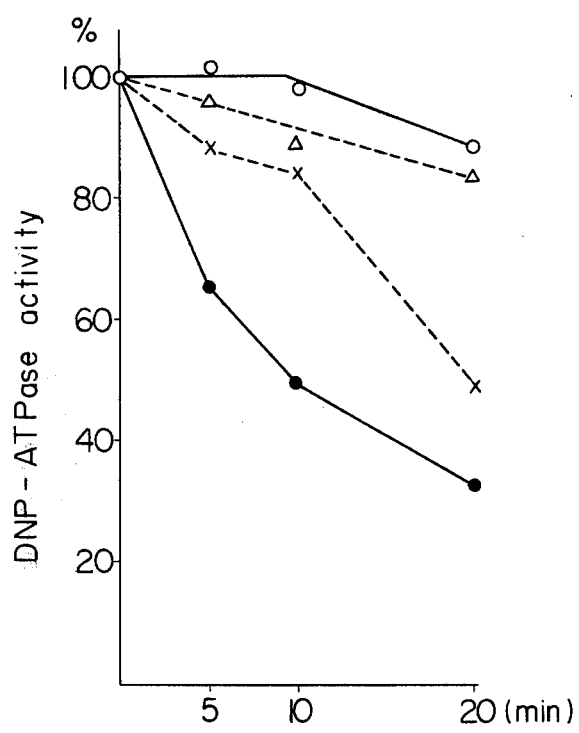
Figure 3A:
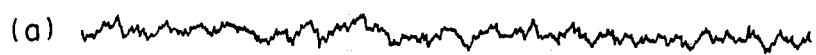
Figure 3A:
Figure 3A:
Figure 3A:
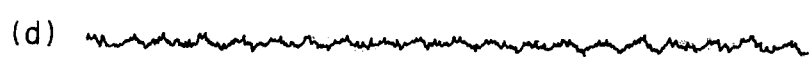
Figure 3A:
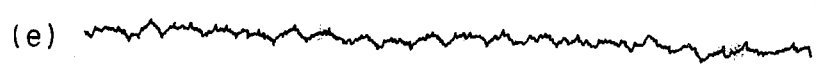
Figure 3A:
Figure 3B:
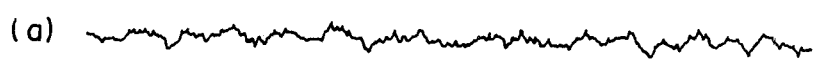
Figure 3B:
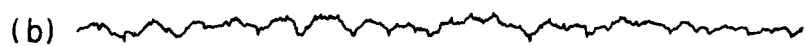
Figure 3B:
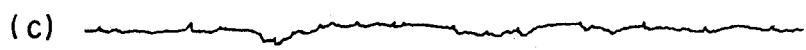
Figure 3B:
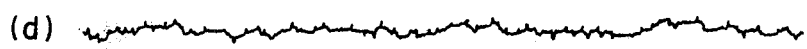
Figure 3B:
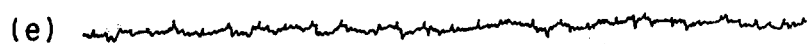
Figure 3B:
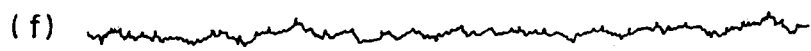

FIG. 2 shows a graph indicating DNP-ATPase-protecting activity of the object substance in which the curves are defined as follows:

| | |
|---|---|
| ———o———: | Object substance (P-IV) prepared with fatty acid treatment in Example (0.1 mg) |
| ———△———: | Active fractions (P-II, III) prepared without fatty acid treatment in Example (5.0 mg) |
| ———x———: | Active fractions (P-II, III) prepared without fatty acid treatment in Example (0.1 mg) |
| ———o———: | Control (added no test substance) |

FIG. 3-(a) shows electroencephalogram of the rats administered intravenously with the object substance according to this invention.

FIG. 3-(b) shows electroencephalogram of the rats administered intraveneously with physiological saline solution as control. In these figures, electroencephalograms (a) through (f) are those measured at the following time:

a. normal conditions
b. under the gas phase of 10% oxygen
c. under the gas phase of 4% oxygen
d. 1 minute after air is introduced
e. 5 minutes after air is introduced
f. 10 minutes after air is introduced The object active substance according to this invention acts to prevent and improve cerebral dysfunction, particularly unconsciousness and cerebral edema induced from head injuries and vascular disorders.

This active substance can be prepared by chemically combining a fatty acid to an albumin, hydrolyzing the modified albumin with the use of a protease and fractionating the hydrolizate in a conventional manner to separate the fraction acting to protect DNP-ATPase activities.

Although any type of albumin may be used as raw substance, egg albumin is preferable from the economical point of view.

The reaction of albumin with a fatty acid is carried out at a temperature of from 30° to 40° C for about 2-5 hours while shaking the reaction system, preferably, in the presence of a surface active agent, such as sodium deoxycholic acid or the like. Examples of fatty acids which may be used in this invention are those having a relatively high molecular weight, such as oleic acid, linoleic acid, stearic acid, palmitic acid, arachidonic acid and the like.

The reaction product, fatty acid-binding albumin, may be recovered from the reaction mixture by a conventional way.

For example, the separation can be carried out by freeze-drying the reaction mixture, suspending the dried material in a small amount of water, centrifuging the suspension at 15,000 r.p.m. for 15 minutes and then subjecting the supernatant to column chromatography using dextran-gel to separate fatty acid-binding albumin from sodium deoxycholic acid and unreacted fatty acid.

As protease for hydrolyzing the fatty acid-binding albumin, pronase which is produced by Streptomyces griseus may be preferably used. This hydrolysis is carried out at a temperature of from 30° to 40° C in a buffer solution adjusted to a pH of 7-8 for 12-36 hours.

The separation of the object substance from the hydrolizate may be carried out in any proper conventional manner, for example, by the use of column chromatography using dextran-gel or a sulfonic acid type ion exhange resin. In case column chromatography is used, the object substance may be obtained by recovering the fractions acting to inhibit deactivation of DNA-ATPase from the eluate with the measurement in a manner similar to that of Yamaguchi et al. (Yamaguchi M., Sato K., Evans J. P. and Ishii S.; Experimental Brain Edema, Arch Neurol., 22; 521-527, 1970) and concentrating the fractions to an appropriate volume under reduced pressure or by freeze-drying.

The present invention will be further explained by the following Example and Experiments, but they are not to be construed as limiting the scope of this invention.

EXAMPLE

Egg albumin (5g) was dissolved in water (50ml), followed by adding active carbon (2.5g: "Darco G-60", produced by Darco Dept. Atlas Powder Co.) to the solution. After adjusting pH of the solution to 3.0 by the addition of 0.1 N HCl, the solution was stirred at 4° C for 1 hour and subjected to centrifugation to precipitate insoluble materials. The pH of the supernatant was adjusted to 7.4 with the use of 0.1N NaOH to obtain 10% egg albumin aqueous solution. To the egg albumin aqueous solution (15 ml) was added 0.04 M phosphate buffer solution (5 ml; pH, 7.4) and an aqueous solution of oleic acid (50 mg) in aqueous sodium deoxycholic acid (50 mg/3 ml). The resulting solution was shaken at 37° C for 3 hours and freeze-dried. The dried product was suspended in water (10 ml) followed by subjecting it to centrifugation at 15,000 r.p.m. for 15 minutes. The supernatant (3 ml) was taken out and subjected to column chromatography (1.7 cm × 100 cm) using Sephadex. The column was eluted with the use of a 0.001 M phosphate buffer solution (pH; 7.4) at an elution rate of 2.5 ml/5 min. The eluate was delivered to a series of test tubes and the fractions having the desired activities were collected (corresponding to test tubes of from Nos. 32 to 45). These fractions contain protein (142.8 mg) and oleic acid (6.97 μg eq.). This fact shows that 10 moles of oleic acid is bound to one mole of egg albumin. Sodium deoxycholic acid and unreacted oleic acid were eluted off in the fractions corresponding to test tubes Nos. 71 and later and completely separated from the oleic acid-binding egg albumin. To the collected fractions (34 ml) containing oleic acid-binding egg albumin was added 0.5M trishydroxymethylaminomethane hydrochloric acid buffer solution (5 ml: pH; 7.4) and then pronase (14mg/10ml) and distilled water (3.0 ml) followed by carrying out the hydrolysis at 37° C for 24 hours. The hydrolizate was subjected to ultrafiltration by the use of Filter-G-05T manufactured from Bioengeneering Kabushiki Kaisha to separate out the substances having a molecular weight less than 5,000 and freeze-drying the substances. The dried powder was dissolved in distilled water (3.4 ml) and the solution was subjected to column chromatography by the use of Sephadex G-25 column (1.7cm × 100cm). The column was developed and eluted with distilled water at a rate of 2.5ml/5 min. to collect the eluate in a series of test tubes. The object substances were confirmed to exist in the fractions corresponding to test tubes Nos. 66-79 by measuring the DNP-ATPase-protecting activity. The total content of the object substances in egg albumin corresponds to about 1 g per 5 g of the albumin.

The eluate distributed to each test tube was assayed by ultraviolet absorption at 280 nm, and absorbancy after ninhydrin color reaction, folin-cioralteu color reaction and Itaya-Ui method (not shown in the Figure) to draw the elution curve by plotting the assay values (FIG. 1-(a)). The fatty acid was specially eluted in fractions Nos. 62-66 (P-III). This special peak corresponding to the fatty acid did not appear in case egg albumin was hydrolyzed by pronase without treatment with the fatty acid (FIG. 1-(b)).

FIG. 1-(a) shows that the object substance was eluted as the fractions corresponding to test tubes Nos. 66-79 (P-IV), while the object substance in the fatty acid-untreated method was in the fractions corresponding to P-II and III (FIG. 2-(b)). The thin layer chromtography gave only one spot as to the object substance according to this invention, while many spots appeared as to the substance according to the fatty acid-untreated method. The results show the substance according to the control test being a mixture of many components. Similarly, the fractions in the portion, P-IV of FIG. 1-(b) comparable in fraction numbers to the fractions P-IV, FIG. 1-(a) containing the object substances were confirmed to be a mixture of many components.

DNP-ATPase-protecting activity was measured using the object substance (P-IV) according to this invention and the substance (P-II and III, FIG. 1-(b)) according to the control test. The results are shown in FIG. 2. As is clear from FIG. 2, the object substance P-IV according to this invention completely protected DNP-ATPase from inactivation in an amount of 0.1 mg, while at least 5 mg of the substance P-II and III of the control test (FIG. 1-(b)) had to be used. Thus, the useful object substance with very high activity could be obtained in high purity and yield by binding a fatty acid with albumin and then hydrolyzing the modified albumin. When the object substance obtained according to this invention is lyophilized it can be stored for a long period of time without losing its effectiveness and the dried substance can be prepared for use as a parenteral injection by dissolving it in a solvent to a desired concentration.

EXPERIMENT 1

DNP-ATPase-protecting activity

Immediately after taking cerebral tissue from two rats, the tissue was homogenated in 20 ml of 0.3M mannitol-0.1M ethylenediamine tetraacetic acid solvent (pH, 7.4) and mitochondria as an about 800 ug/ml protein aqueous solution was prepared by a method in accordance with Ozawa et al. (Ozawa K, Seta K, Takeda H, and Araki C; On the isolation of mitochondria with high respiratory control from rat brain; J. Biochem., 59 501-509, 1966). To the solution of mitochondria (0.1 ml) was added 0.9 ml of the solvent used above (control), 0.9 ml of the solvent containing the object substance of this invention (FIG. 1-(a) peak IV) or the substance (FIG. 1-(b) peak II and III), and the mixture was incubated at 20° C for 0.5, 10, or 20 min. Then, DNP-ATPase activity was determined.

The determination of enzyme activity was carried out by mixing 2.5M KCl (2ml), 0.5M trishydroxymethylaminomethane hydrochloric acid buffer solution (10 ml; pH, 7.4), 10 mM dinitrophenol (2ml) and 0.2M adenosine triphosphate (3 ml) with distilled water to prepare 20 ml total amount of a substrate buffer solution. To the substrate solution (0.2 ml) was added distilled water (0.7 ml) and then the enzyme solution (0.1 ml), and the mixture was subjected to reaction at 30° C for 10 min. The reaction was terminated by addition of 15% trichloroacetic acid (0.1 ml) and, at the same time, the reaction mixture was centrifuged. Inorganic phosphorus in the supernatant free from protein was quantitatively analyzed by the Fiske-Subarrow method.

The results are shown in FIG. 2.

EXPERIMENT 2

Normalizing effect of high-voltage abnormal electroencephlogram (EEG) and consciousness disturbance recovering effect Four rats were used in this experiment. A rubber tube was connected through an outlet with a air-tight box which has an openable door and has an inlet connected with a nitrogen gas feeder. The rubber tube was branched, the opposite ends of the two paths being connected to a rat fixed with gallamine triethiodide through tracheotomy tube whereby gas same in composition and pressure as that in the box can be simultaneously charged into the body of two rats. Further, an electrode for EEG was placed on the top of head of each rat in order to realize the simultaneous recording of EEG.

When the EEG of the rats had returned to normal state, one of the rats was injected intravenously through a vein of tail with physiologically saline solution and the other with the object substance prepared in Example according to this invention. At the same time, untreated rats one of which was injected with physiological saline solution and the other of which was administered with the object substance were placed in the air-tight box and the door of the box was closed to seal it. Immediately after the door of the box was closed, nitrogen gas was fed into the box to gradually lower the partial pressure of oxygen in the box while behavior of the rats in the box was observed and EEG of rats fixed with gallamine triethiodide was simultaneously recorded. When the atmosphere in the box was under ischemic conditions and the rats in the box lay on their backs, the door of the box was opened to let air enter into the box at once. The recovery of the rats were observed in view of the symptoms and EEG changes.

The change of the EEG is shown in FIG. 3. Table 1 shows the results of this experiment in which the period of time required until righting reflex returned to positive was measured as an index of recovery of the cerebral function. Other symptoms were observed and recorded on the film.

From the results observed, it is confirmed that the substance contained in the fractions corresponding to FIG. 1-(a), peak IV has activity for accelerating the recovery of cerebral function after disorder is induced by anoxia and that, in a group of rats administered with the substance (FIG. 1-(a), peak IV), the time for appearing cyanose during anoxia was prolonged.

The experiments described above were repeated except that the test substance was intravenously injected through a tail vein after the rats were taken out from the box to prove that the similar activity for accelerating recovery from cerebral function disorder was observed.

Table 1

Activity for accelerating restoration of ischemic rat by the substance separated and purified from the hydrolyzate of fatty acid-binding egg albumin.

| | | Period required until righting reflex returned to positive | |
|---|---|---|---|
| Control | 1 | 4 (min.) | 40 (sec.) |
| | 2 | 2 | 50 |
| | 3 | 1 | 20 |
| | 4 | 4 | 15 |
| | 5 | 3 | 55 |
| | 6 | 3 | 05 |
| | Average | 3 | 42 |
| Administered the fractions FIG. 1-(a), peak IV | 1 | | 40 |
| | 2 | 1 | 03 |
| | 3 | 1 | 15 |
| | 4 | | 50 |
| | 5 | | 40 |
| | 6 | | 55 |
| | Average | | 54 |

What I claim is:

1. A process for manufacturing a preparation for normalizing electroencephalogram abnormalities and consciousness disturbance induced by anoxia, having the following properties:
    Appearance and Properties: colorless and odorless
    Solubility: easily soluble in water, hardly soluble in alcohol, acetone and ether
    Stability: stable at room temperature, stable under freezing and defrosting
    Ultraviolet Absorption Spectrum: maximum absorption at 280 nm
    Molecular Weight: 1000 ~ 3000
    Color reaction: positive in ninhydrin
    Thin layer Chromatography:
        RF = 0.355 ± 0.075
        Plate: microcrystalline cellulose
        Developing Solvent: n-butanol:acetic acid:water = 3:1:1
        Conditions for Developing: room temperature
    Color Reaction: ninhydrin,
comprising the steps of:
   1. adding a fatty acid of 16-20 carbon atoms to an aqueous albumin solution in an amount sufficient to cause conjugation, said albumin being selected from the group consisting of egg albumin and bovine serum albumin, thereby reacting the albumin with the fatty acid to form modified albumin;
   2. collecting the modified albumin, dissolving the modified albumin in a small amount of water to form an aqueous modified albumin solution, and adding pronase thereto, thereby hydrolyzing the modified albumin; and
   3. carrying out a column chromatography using dextran gel or sulfonic acid type ion exchange resin having a molecular weight fractionation range of 1,000 - 5,000 and collecting the fraction acting to inhibit deactivation of DNP-ATPase.

2. A process in accordance with claim 1, wherein said albumin is egg albumin.

3. A process in accordance with claim 1, wherein said fatty acid is selected from the group consisting of oleic acid, linoleic acid, stearic acid, palmitic acid and arachidonic acid.

4. A process in accordance with claim 1, wherein said reaction of albumin with a fatty acid is carried out at a temperature of from 30° to 40° C for about 2 - 5 hours while shaking the reaction system.

5. A process in accordance with claim 5, wherein said reaction is carried out in the presence of a surface active amount of sodium deoxycholic acid.

6. A process in accordance with claim 1, wherein, in said step (2), said pronase is added at a temperature of from 30° to 40° C in a buffer solution adjusted to a pH of 7-8 and maintained for 12-36 hours.

7. The product prepared by the process of claim 1.

UNITED STATES PATENT AND TRADEMARK OFFICE
CERTIFICATE OF CORRECTION

PATENT NO. : 4,067,963
DATED : January 10, 1978
INVENTOR(S) : ISHII, Shozo

It is certified that error appears in the above-identified patent and that said Letters Patent are hereby corrected as shown below:

Column 1, line 58, "RF" should read --Rf--

Column 2, line 11, "(P-1V)" should read --(P-IV)--

Column 3, line 13, "Arch Neurol., 22" should read --Arch Neurol., $\underline{22}$--

Column 4, line 5, "folin-cioralteu" should read --folin-chioralteu--

Column 4, line 17, "chromtography" should read --chromatography--

Column 4, line 52, "ug/ml" should read --µg/ml--

Column 6, line 32 "RF" should read --Rf--

Signed and Sealed this

Twenty-ninth Day of August 1978

[SEAL]

Attest:

RUTH C. MASON
Attesting Officer

DONALD W. BANNER
Commissioner of Patents and Trademarks